United States Patent [19]

Regnier et al.

[11] Patent Number: 4,514,398
[45] Date of Patent: Apr. 30, 1985

[54] DISUBSTITUTED POLYMETHYLENE IMINES

[75] Inventors: Gilbert Regnier, Chatenay-Malabry; Alain Dhainaut, Chatou; Michel Laubie, Vaucresson; Jacques Duhault, Croissy s/Seine, all of France

[73] Assignee: ADIR, Neuilly-sur-Seine, France

[21] Appl. No.: 478,715

[22] Filed: Mar. 25, 1983

[30] Foreign Application Priority Data

Mar. 30, 1982 [FR] France ................. 82 05373

[51] Int. Cl.³ ............... C07D 401/04; C07D 403/04; A61K 31/53
[52] U.S. Cl. ............................ 514/245; 544/198
[58] Field of Search ............ 544/198; 542/423, 425; 424/249

[56] References Cited

U.S. PATENT DOCUMENTS 3,576,805  4/1971  Cantrall et al. ................ 544/198

OTHER PUBLICATIONS

IUPAC, Nomenclature of Organic Chemistry, Sec. A, p. 21; Sec. B, p. 51; 2nd Edition, Jul. 1957, Butterworths Pub., London.
IUPAC, Nomenclature of Organic Chemistry, Section C, p. 105, (1965), Butterworths Pub., London.
Merck Index, p. 1081, Merck & Co., Rahway, N.J., (1983).
Hamburger, "Dictionnaire de Medecine," Flammarion Medecine–Sciences, Paris, p. 407 (1982).
Chemical Abstracts "The Naming and Indexing of Chemical Compounds" p. 88N, (1962).

Primary Examiner—John M. Ford
Attorney, Agent, or Firm—Gordon W. Hueschen

[57] ABSTRACT

Polymethylene-imines of the formula:

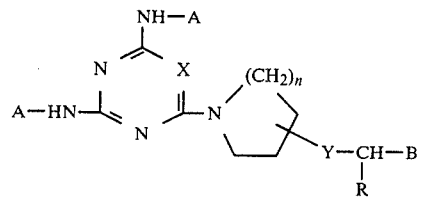

in which:

A is a hydrocarbon radical from $C_3$ to $C_5$ in a straight or branched chain possibly containing one or two double bonds and possibly substituted by one or more hydroxy radicals;

X is CH or nitrogen;

n is zero, one or two;

Y is oxygen or N—$R_1$ in which $R_1$ is hydrogen, alkyl from $C_1$ to $C_5$, alkenyl from $C_2$ to $C_5$, cycloalkyl or cycloalkenyl from $C_3$ to $C_7$, or acetyl;

R is hydrogen, alkyl from $C_1$ to $C_5$, cycloalkyl from $C_5$ to $C_7$ or phenyl optionally substituted by one or more fluorine or chlorine; and B is hydrogen, alkyl from $C_1$ to $C_5$, alkenyl from $C_2$ to $C_5$, or phenyl, naphthyl, benzofuranyl, benzothienyl, benzodioxolyl, benzodioxanyl, benzodioxinyl, Δ3-chromanyl, thiochromenyl or chromanyl, each optionally substituted by fluorine, chlorine, alkyl or alkoxy from $C_1$ to $C_5$; or a radical of the formula:

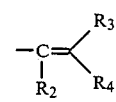

in which:

$R_2$, $R_3$ and $R_4$ which may be the same or different, each represent hydrogen, or phenyl optionally substituted by fluorine or chlorine.

These compounds and physiologically tolerable acid addition salts thereof may be used as medicines especially in the treatment of all kinds of tissular hypoxia.

8 Claims, No Drawings

DISUBSTITUTED POLYMETHYLENE IMINES

The present invention provides disubstituted polymethylene-imines of the formula:

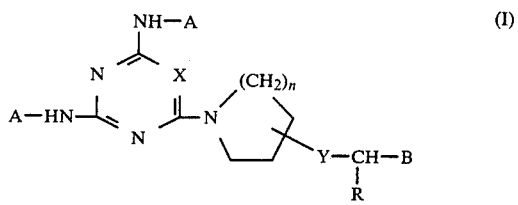

in which:

A is selected from the group consisting of saturated hydrocarbon radical containing from 3 to 5 carbon atoms inclusive in straight and branched chain, the corresponding unsaturated hydrocarbon radicals containing one and two double bonds, and the corresponding mono- and di-hydroxy (saturated and unsaturated) hydrocarbon radicals;

X is selected from the group consisting of —CH— and a nitrogen atom;

n is selected from the group consisting of zero and the integers 1 and 2;

Y is selected from the group consisting of an oxygen atom and a radical of the formula: N—$R_1$ in which $R_1$ is selected from the group consisting of: a hydrogen atom, alkyl and hydroxyalkyl radicals each having from 1 to 5 carbon atoms inclusive, alkenyl radicals having from 2 to 5 carbon atoms inclusive, cycloalkyl and cycloalkenyl radicals each having from 3 to 7 carbon atoms inclusive, and an acetyl radical, R is selected from the group consisting of: a hydrogen atom, alkyl radicals having from 1 to 5 carbon atoms inclusive, cycloalkyl radicals having from 5 to 7 carbon atoms inclusive, an unsubstituted phenyl radical and phenyl radicals mono- and poly-substituted by a substituent selected from the group consisting of fluorine and chlorine atoms; and B is selected from the group consisting of:

a hydrogen atom;

alkyl radical having from 1 to 5 carbon atoms inclusive;

alkenyl radicals having from 2 to 5 carbon atoms inclusive;

phenyl, naphthyl, benzofuranyl, benzothienyl, benzodioxolyl, benzodioxanyl, benzodioxinyl, Δ3-chromenyl, thiochromenyl and chromanyl radicals and all these radicals mono- and poly-substituted by a substituent selected from the group consisting of: fluorine and chlorine atoms and alkyl and alkoxy radicals each having from 1 to 5 carbon atoms inclusive; and a radical of the formula:

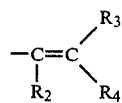

in which $R_2$, $R_3$ and $R_4$ which may be the same or different are each selected from the group consisting of: a hydrogen atom, an unsubstituted phenyl radical and phenyl radicals mono- and poly-substituted by a substituent selected from the group consisting of chlorine and fluorine atoms.

The present invention further provides a process for preparing the compounds of the formula I, in which:

a disubstituted polymethylene-imine of the general formula II:

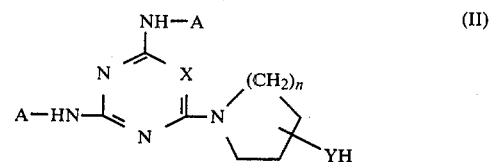

in which A, n, X, and Y have the definitions previously stated;

is condensed with a halo compound of the general formula III:

in which R and B have the previously defined significance and Hal represents a halogen atom, such for example as a chlorine or bromine atom.

The condensation is preferably carried out in a solvent chosen from the benzene hydrocarbons with high boiling point such as toluene or xylene, the aliphatic amides such as dimethylformamide or dimethylacetamide, possibly mixed with a high boiling point benzene hydrocarbon, or methyl cyanide. It is advantageous to operate at a temperature between 120° and 140° C. in the presence of an acceptor of the hydracid formed during the reaction. This acceptor can be chosen from the alkaline carbonates such as potassium carbonate, triethylamine or an excess of polymethylene-imine of the formula II used for the condensation.

The present invention also provides the process for preparing the compounds of the general formula I':

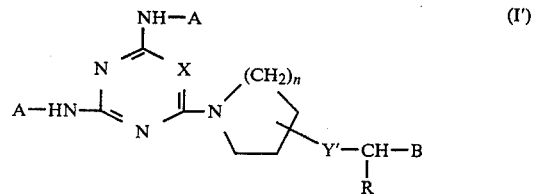

in which:

A, X, n, R and B are as previously defined and

Y' represents an oxygen atom or a radical —N—$R'_1$ in which $R'_1$ is selected from the group consisting of alkyl and hydroxy alkyl radicals each having from 1 to 5 carbon atoms inclusive, alkenyl radicals from 2 to 5 carbon atoms, and cycloalkyl and cycloalkenyl radicals each having from 3 to 7 carbon atoms and an acetyl radical inclusive, characterised in that:

a halo compound of the general formula IV:

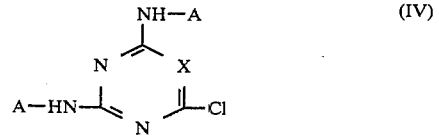

in which A and X have the previously defined significances, is condensed with a mono-substituted polymethylene-imine of the general formula V:

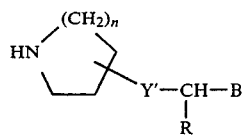

in which n, R, Y', and B are as previously defined.

The condensation is carried out in a particularly adequate manner in a solvent chosen from the alcohols in C$_4$ or C$_5$ such as butanol or pentanol, and the aliphatic amides like dimethylformamide or dimethylacetamide. It is recommended to operate at a temperature between 120° and 150° C. in the presence of an acceptor of the hydracid formed in the course of the reaction. This acceptor can be chosen from an excess of the imine of the general formula V previously defined, triethylamine, or the alkaline carbonates such as potassium carbonate.

The present invention also provides the process for preparing the compounds of the general formula I":

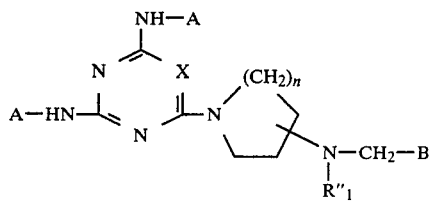

in which:

A, X, n, and B are as previously defined, and

R"$_1$ is selected from the group consisting of a hydrogen atom, alkyl and hydroxyalkyl radicals each having from 1 to 5 carbon atoms inclusive, alkenyl radicals having from 2 to 5 carbon atoms inclusive and cycloalkyl and cycloalkenyl radicals each having from 3 to 7 carbon atoms inclusive, characterised in that:

the corresponding amide with the general formula VI:

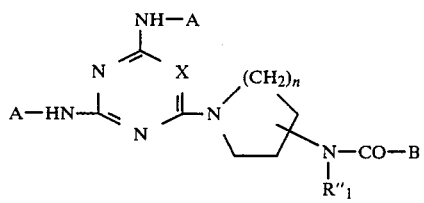

in which A, X, n, R"$_1$ and B are as previously defined, is reduced.

As reducing agent there can be used for example the double hydride of lithium aluminium: Li Al H$_4$ or the hydride of boron: B$_2$H$_6$.

A particularly suitable method of working consists in carrying out the reduction in a solvent such as tetrahydrofuran at a temperature between 20° and 60° C.

The present invention also provides the process for preparing the compounds of the general formula I''':

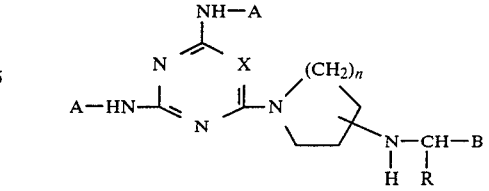

in which:

A, X, n, R and B have the previously defined significances, characterised in that a mixture of the ketone of the formula VII:

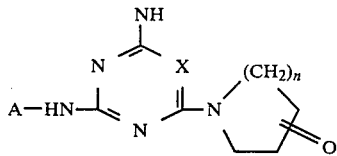

in which A, X and n are as previously defined and an amine of the formula VIII:

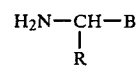

in which R and B are as previously defined, is treated with sodium cyanoborohydride.

It is particularly advantageous to operate in a suitable solvent such for example as methanol or tetrahydrofuran at a temperature between 20° and 25° C., at a pH near to 6.

These new compounds so obtained can be converted into salts of addition with acids, salts which by this fact form part of the invention. As acids which may be used for the formation of these salts, there may be cited for example in the mineral series hydrochloric, hydrobromic, sulfuric, and phosphoric acids and in the organic series, acetic, propionic, maleic, fumaric, tartaric, nitric, oxalic, benzoic, methanesulfonic and isethionic acids.

These new compounds can be purified by physical methods such as crystallisation, chromatography, or chemical methods such as the formation of salts of addition with acids and decomposition of these salts by alkaline agents.

The raw materials utilised in the previously described processes are either known products, or products prepared starting from known substances, according to the processes described to prepare similar products as indicated in the following examples.

The compounds of the general formula I and their physiologically tolerable addition salts possess interesting pharmacological and therapeutical properties. In particular, they favour the capturing of oxygen and thus enable them to be used as a medicine, notably in the treatment of all kinds of tissular hypoxia.

These derivatives and their physiologically tolerable salts furthermore present a very weak toxicity.

The effect of these derivatives according to the invention on the oxygen pressure (PO$_2$) has been studied in dogs anaesthetised with Nembutal. Blood samples are taken periodically 2, 5, 15, 45 and 75 minutes after the administration of the compounds under test; they serve for the determination of the pH, of the $PO_2$ and of the $PCO_2$.

The $PO_2$ is measured on a radiometer $BMS_3$ apparatus. The reading of the $PO_2$ is done on this apparatus which has previously been calibrated with known values, by means of a platinum electrode, or a Clark electrode.

The products have been administered to the dog by intravenous route at the rate of 1 mg/kg and the determination of the percentage increase in the oxygen content of the arterial blood shows that this percentage, depending on the compounds, can reach up to 37%, 75 minutes after the administration of the compound.

The products of the present invention were also shown to be active in the treatment of anemic hypoxia induced by chemical route with a sub-cutaneous injection of $NaNO_2$, according to Gibson G. E's method, Neurobiol. Aging 2, 165, (1981) and Biochem. Pharmacol. 28, 747, (1979) and in hypobaric hypoxia according to the technic of Legeai J. M. and als, Experientia 37, 292, (1981).

The present invention also provides the pharmaceutical compositions containing as active principle a compound of the general formula I or a physiologically tolerable salt thereof mixed or associated with a suitable pharmaceutical excipient.

It is particularly concerned with the forms containing doses from 20 to 100 mg of active principle.

The pharmaceutical composition so obtained are advantageously presented in the various dosed forms such for example as tablets, sugar-coated tablets, capsules, suppositories, injectable or drinkable solutions. They can be administered by oral, rectal or parenteral route at doses from 20 to 100 mg once to twice a day.

The following examples illustrate the invention without limiting it.

EXAMPLE 1

1-(4,6-bis allylamino s.triazin-2-yl)-4-(bis p.fluoro-benzhydrylamino)-piperidine

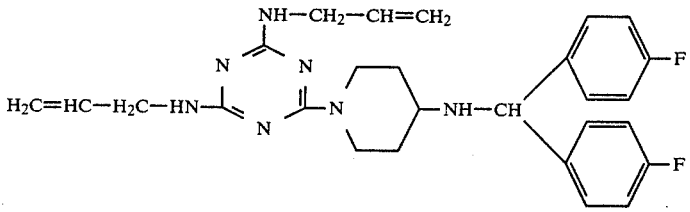

A solution of 12.4 g of 1-(4,6-bis allylamino s.triazin-2-yl)-4-amino piperidine, melting (capillary) at 118°-120° C., and 4.04 g of bis(p.fluorophenyl)-bromomethane in 100 ml of $H_3CCN$ is heated at reflux for 2 hours. After leaving for one night at ordinary temperature the hydrobromide crystals are filtered and the solution is evaporated under reduced pressure. The expected product is separated from the excess of starting base by filtering the oily residue obtained in solution in ethyl acetate on a silica column. Starting from the product obtained after evaporation of the eluates, the fumarate is prepared in ethanol and 5.2 g of white crystals of difumarate of 1-(4,6-bis allylamino s.triazin-2-yl-4-(bis p.fluorobenzhydrylamino)piperidine, are obtained, melting (capillary) at 208°-210° C.

The starting amino piperidine has been prepared by reduction with $LiAlH_4$ in tetrahydrofuran of the corresponding oxime melting (capillary) at 180° C., itself prepared starting from 1-(4,6-bis allylamino s.triazin-2-yl piperidine, M.P. (capillary) of the corresponding hydrochloride: 219°-222° C., itself prepared starting from the 4,6-bis allylamino-2-chloro s.triazine, and 4,4-diethoxy piperidine, in the presence of potassium carbonate.

EXAMPLES 2 TO 19

The following compounds have been prepared by the method described in example 1.

(2) 1-(4,6-bis allylamino s.triazin-2-yl)-4-p.fluorobenzylamino piperidine, of which the difumarate melts (Kofler) at 242° C. (anhydrous ethanol).

(3) 1-(4,6-bis allylamino s.triazin-2-yl)-4-(benzofuran-2-yl methylamino)piperidine of which the difumarate (Kofler) melts at 207° C. (anhydrous ethanol).

(4) 1-(4,6-bis allylamino s.triazin-2-yl)-4-benzhydrylamino piperidine, of which the difumarate melts (capillary) at 227° C. (ethanol).

(5) 1-(4,6-bis allylamino s.triazin-2-yl)-4-(α-cyclohexyl p.fluorobenzylamino piperidine, of which the difumarate melts (Kofler) at 228° C. (anhydrous ethanol).

(6) 1-(4,6-bis allylamino s.triazin-2-yl)-4-piperonylamino piperidine of which the difumarate (Kofler) melts ar 227° C. (anhydrous ethanol).

(7) 1-(4,6-bis crotylamino s.triazin-2-yl)-4 (bis p.fluorobenzhydrylamino)piperidine, of which the dihydrochloride melts (Kofler) at 228°-230° C.

(8) 1-(2,4-bis allymino pydimidin-6-yl)-4-(bis p.fluorobenzhydrylamino)piperidine, of which the dihydrochloride melts at 240° C. (anhydrous ethanol).

(9) 1-(4,6-bis allylamino s.triazin-2-yl)-4-(N-bis p.fluorobenzhydryl N-ethyl amino)piperidine, of which the difumarate (Kofler) melts at 163° C. (anhydrous ethanol).

(10) 1-(4,6-bis allylamino s.triazin-2-yl)-4-p.fluorobenzhydrylamino piperidine, of which the dihydrochloride melts (Kofler) at 242° C. (anhydrous ethanol).

(11) 1-(4,6-bis allylamino s.triazin-2-yl)-4-(Δ3-chromen-3-yl methylamino)piperidine, of which the dihydrochloride melts (Kofler) at 220° C., (anhydrous ethanol).

(12) 1-(4,6-bis allylamino s.triazin-2-yl)-4-cynnamylamino piperidine, of which the dihydrochloride melts (Kofler) at 195° C. (anhydrous ethanol).

(13) 1-(4,6-bis allylamino s.triazin-2-yl)-4 (4-fluoronaphth-1-yl methylamino)piperidine of which the difumarate melts (Kofler) at 217° C. (anhydrous ethanol).

(14) 1-(4,6-bis allylamino s.triazin-2-yl)-4-(bis p.fluorobenzhydryloxy)piperidine, of which the hydrochloride melts (capillary) at 182°-184° C. (ethanol).

(15) 1-(4,6-bis allylamino s.triazin-2-yl)-4-ethoxy piperidine, of which the difumarate melts (Kofler) at 188° C. (anhydrous ethanol).

(16) 1-(4,6-bis allylamino s.triazin-2-yl)-4-(benzothien-2-yl methylamino)piperidine, of which the difumarate melts (Kofler) at 220° C. (ethanol at 95%).

(17) 1-(4,6-bis allylamino s.triazin-2-yl)-3-(bis p.fluorobenzhydrylamino)piperidine.

(18) 1-(4,6-bis allylamino s.triazin-2-yl)-3-(bis p.fluorobenzhydrylamino)azetidine.

(19) 1-(4,6-bis allylamino s.triazin-2-yl)-4-(bis p.fluorophenyl allylamino)piperidine.

EXAMPLE 20

1-(4,6-bis allylamino s.triazin-2-yl)-4-(N-bis p.fluorobenzhydryl N-ethylamino)piperidine

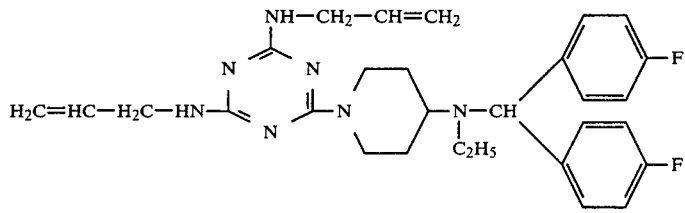

A solution of 4,6 g of 4,6-bis allylamino-2-chloro s.triazine and 7.8 g of 4-(N-ethyl N-bis p.fluorobenzhydryl amino)piperidine in 150 ml of n.butanol is heated for 7 hours at reflux in the presence of 2.02 g of triethylamine. At the end of this time, the solution is cooled and evaporated under reduced pressure; the gelatinous residue obtained is treated with 250 ml of benzene and washed four times with 50 ml of water. After decanting and evaporation of the benzene, 110 g of residual oil is obtained of which the fumarate is prepared in ethanol. 11.2 g of difumarate melting (capillary) at 163° C. is obtained.

The starting amino piperidine (B.P./0.075 mm of Hg: 190°-200° C.), has been prepared by deacetylation by means of sodium hydroxide in ethanol of 1-acetyl-4-(N-ethyl, N-bis p.fluorobenzhydryl amino)piperidine (oil), itself prepared by condensation in acetonitrile of bis p-fluorobenzhydryl bromide and 1-acetyl-4-ethylaminopiperidine ((MP/15 mm HG: 155°-160° C.).

EXAMPLES 21 TO 26

The following compounds have been prepared by the method described in example 20:

(21) 1-(4,6-bis allylamino s.triazin-2-yl)-4-(N-bis p.fluorobenzhydryl N-allylamino)piperidine.

(22) 1-(4,6-bis allylamino s.triazin-2-yl)-4-(N-bis p.fluorobenzhydryl N-cyclohexylamino)piperidine.

(23) 1-(4,6-bis allylamino s.triazin-2-yl)-4-(N-bis p.fluorobenzhydryl N-hydroxyethylamino)piperidine.

(24) 1-(4,6-bis allylamino s.triazin-2-yl)-4-(N-cinnamyl N-ethylamino)piperidine, M.P. (Kofler) of the corresponding difumarate: 168°-170° C. (anhydrous ethanol).

(25) 1-(4,6-bis n.propylamino s.triazin-2-yl)-4-bis p.fluorobenzhydrylamino piperidine, M.P. (capillary) of the corresponding difumarate: 222°-225° C. (anhydrous ethanol).

(26) 1-(4,6-bis allylamino s.triazin-2-yl)-4-(4-fluoro naphth-1-yl acetylamino)piperidine, M.P. (capillary) of the corresponding fumarate: 147°-152° C. (anhydrous ethanol).

EXAMPLE 27

-1-(4,6-bis allylamino s.triazin-2-yl)-4-bis p.fluorobenzhydryloxy piperidine

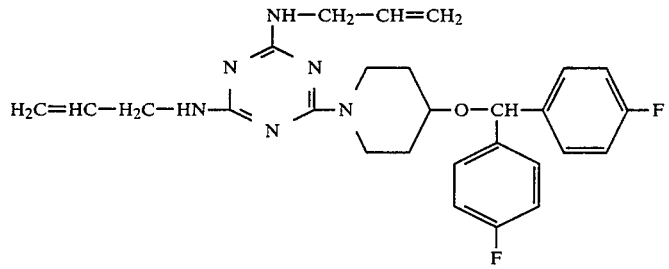

A solution of 2.25 g of 4,6-bis allylamino-2-chloro triazine and 3 g of 4-bis p.fluorobenzhydryloxy piperidine in 50 ml of butanol is heated for 6 hours at reflux, in the presence of 1.4 ml of triethylamine. At the end of this time the solvent is evaporated. The residue is taken up by 100 ml of ether and the solution is washed with 100 ml of a solution at 10% of sodium carbonate and then with twice 50 ml of water. After decanting and evaporation of the ether, a residual oil is obtained from which the hydrochloride is prepared in ethanol. 2.1 g of 1-(4,6-bis allylamino s.triazin-2-yl)-4-bis p.fluorobenzhydryloxy piperidine hydrochloride melting (capillary) at 182°-184° C., is isolated.

The 4-bis p.fluorobenzhydryloxy piperidine, of which the oxalate melts (capillary) at 182°-184° C., has been prepared by condensation of the bis p.fluorobenzhydryl bromide with 1-acetyl piperidin-4-ol in tetrahydrofuran in the presence of sodium hydride.

EXAMPLES 28 TO 39

The following compounds have been prepared by the method described in example 27:

(28) 1-(4,6-bis allylamino s.triazin-2-yl-4-ethoxy piperidine, M.P. (Kofler) of the corresponding difumarate: 188° C. (anhydrous ethanol).

(29) 1-(4,6-bis allylamino s.triazin-2-yl)-4-methoxy piperidine, M.P. (Kofler) of the corresponding fumarate: 193° C. (ethanol).

(30) 1-(4,6-bis allylamino s.triazin-2-yl)-4-allyloxy piperidine, M.P. (Kofler) of the corresponding fumarate: 184° C. (ethanol).

(31) 1-(4,6-bis allylamino s.triazin-2-yl)-4-n.butoxy piperidine, M.P. (Kofler) of the corresponding fumarate: 183° C. (ethanol).

(32) 1-(4,6-bis allylamino s.triazin-2-yl)-4-n.propoxy piperidine, M.P. (Kofler) of the corresponding fumarate: 195° C. (anhydrous ethanol).

(33) 1-(4,6-bis allylamino s.triazin-2-yl)-4-cinnamyloxy piperidine, M.P. (Kofler) of the corresponding fumarate: 165° C. (ethanol).

(34) 1-(4,6-bis allylamino s.triazin-2-yl)-4-p.fluorocinnamyloxy piperidine, M.P. (Kofler) of the corresponding fumarate: 152° C. (anhydrous ethanol).

(35) 1-(2,4-bis allylamino pyrimidin-6-yl)-4-ethoxy piperidine, M.P. (Kofler) of the corresponding fumarate: 158° C. (anhydrous ethanol).

(36) 1-(4,6-bis allylamino s.triazin-2-yl)-4-benzothien-2-yl methoxy)piperidine, M.P. (Kofler): 110° C. (acetonitrile).

(37) 1-(4,6-bis allylamino s.triazin-2-yl)-3-ethoxy piperidine, M.P. (Kofler) of the corresponding fumarate: 152° C. (anhydrous ethanol).

(38) 1-(4,6-bis allylamino s.triazin-2-yl)-3-ethoxy pyrrolidine, M.P. (capillary) of the corresponding fumarate: 148°–150° C. (anhydrous ethanol).

(39) 1-(4,6-bis allylamino s.triazin-2-yl)-3-ethoxy azetidine, M.P. (Kofler): 96° C.

EXAMPLE 40

1-(4,6-bis allylamino s.triazin-2-yl)-4-(benzofuran-2-yl methylamino)piperidine:

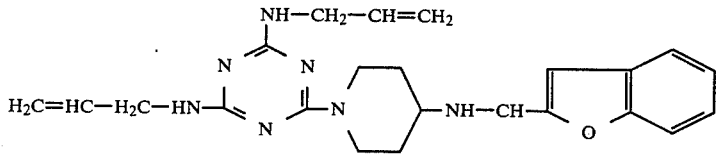

A solution of 8 g of 1-(4,6-bis allylamino s.triazin-2-yl)-4-(benzofuran-2-yl carbonamido)piperidine, melting (Kofler) at 160° C., in 250 ml of tetrahydrofuran is heated for 30 hours at reflux in the presence of 4.2 g of lithium alanate. After cooling to 0° C. there are added successively under nitrogen, 4 ml of water, 8 ml of a 2N solution of sodium hydroxide and 12 ml of water; the precipitate of alumimium formed is separated, rinced several times with tetrahydrofuran and the filtrate is evaporated to dryness. An oil is obtained which is taken up by CH2Cl2 and dried on Na2SO4. The solvent is again evaporated, and 7.2 g of a yellow oil is obtained which is purified by filtration of its solution in ethyl acetate on silica. The evaporated eluates give 3 g of product which is converted into the fumarate in ethanol. Finally 4.1 g of difumarate of 1-(4,6-bis allylamino s.triazin-2-yl-4-(benzofuran-2-yl methylamino)piperidine is isolated in the form of white crystals melting (Kofler) at 207° C.

The starting amide has been prepared by the addition of 2-benzofuran carboxylic acid chloride to 1-(4,6-bis allylamino s.triazin-2-yl)-4-amino piperidine, (of which the dihydrochloride melts above 260° C.), in tetrahydrofuran in the presence of triethylamine.

EXAMPLES 41 TO 46

The following compounds have been prepared according to the method described in example 40:

(41) 1-(4,6-bis allylamino s.triazin-2-yl)-4-p.fluorobenzylamino piperidine, M.P. (Kofler) of the corresponding difumarate: 242° C. (anhydrous ethanol).

(42) 1-(4,6-bis allylamino s.triazin-2-yl)-4-piperonylamino piperidine, M.P. (Kofler) of the corresponding difumarate: 227° C. (anhydrous ethanol).

(43) 1-(4,6-bis allylamino s.triazin-2-yl)-4-(Δ3-chromen-3-yl methylamino)piperidine, M.P. (Kofler) of the corresponding dihydrochloride: 250° C. (anhydrous ethanol).

(44) 1-(4,6-bis allylamino s.triazin-2-yl)-4-cynnamylamino piperidine M.P. (Kofler) of the corresponding dihydrochloride: 195° C. (anhydrous ethanol).

(45) 1-(4,6-bis allylamino s.triazin-2-yl)-4-(4-fluoro naphthyl-1-yl methylamino)piperidine, M.P. (Kofler) of the corresponding difumarate: 217° C. (anhydrous ethanol).

(46) 1-(4,6-bis allylamino s.triazin-2-yl)-4-(benzothien-2-yl methylamino)piperidine, M.P. (Kofler) of the corresponding difumarate: 220° C. (ethanol at 95%).

EXAMPLE 47

1-(4,6-bis allylamino s.triazin-2-yl)-4-bis p.fluorobenzhydrylamino piperidine:

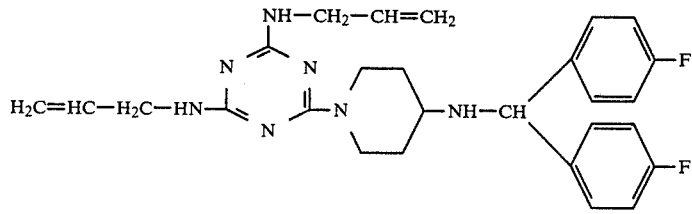

2 g of molecular sieve (3 Å) and 1.25 g of sodium cyanoborohydride are added to a solution of 6.5 g of 1-(4-bis allylamino s.triazin-2-yl)-4-piperidone melting (capillary) at 219°–222° C. and of 6.6 g of bis p.fluorobenzhydrylamine (MP/0.005 mm Hg: 140°–145° C.; $n_D^{21}$ 1.555) in 80 ml of anhydrous methanol. The pH of the suspension obtained is adjusted to 6 by means of a 4N solution of HCl in methanol and the mixture is stirred for 18 hours at room temperature. At the end of this time, the solvent is evaporated and the residue is treated with 200 ml of chloroform and 200 ml of 10% sodium bicarbonate. After decanting, the chloroform is evaporated and the oily residue weighing 9 g is converted into the difumarate in ethanol. 9.8 g of 1-(4,6-bis allylamino s.triazin-2-yl-4-bis p.fluorobenzhydrylamino piperidine difumarate are obtained in the form of beige-coloured crystals, melting (capillary), at 208°–210° C.

The starting bis p.fluorobenzhydrylamine has been prepared by reduction of the oxime of bis p.fluorobenzophenone, melting at 128° C., by hydrogen in the presence of Raney's nickel under a pressure of 50 atmospheres.

EXAMPLES 48 TO 68

The following compounds have been prepared according to the process described in example 47.

(48) 1-(4,6-bis allylamino s.triazin-2-yl)-4-p.fluorobenzylamino-piperidine, M.P. (Kofler) of the corresponding difumarate: 242° C. (anhydrous ethanol).

(49) 1-(4,6-bis allylamino s.triazin-2-yl)-4-(benzofuran-2-yl methylamino)-4-piperidine, M.P. (Kofler) of the corresponding difumarate: 207° C. (anhydrous ethanol).

(50) 1-(4,6-bis allylamino s.triazin-2-yl)-4-benzyhydrylamino piperidine, M.P. (capillary) of the corresponding difumarate: 227° C. (ethanol).

(51) 1-(4,6-bis allylamino s.triazin-2-yl)-4-(α-cyclohexyl p.fluorobenzylamino)piperidine, M.P. (Kofler) of the corresponding difumarate: 228° C. (anhydrous ethanol).

(52) 1-(4,6-bis allylamino s.triazin-2-yl)-4-piperonylamino piperidine, M.P. (Kofler) of the corresponding difumarate: 227° C. (anhydrous ethanol).

(53) 1-(4,6-bis crotylamino s.triazin-2-yl)-4-bis p.fluorobenzhydrylamino piperidine, M.P. (Kofler) of the corresponding dihydrochloride: 228°–230° C.

(54) 1-(2,4-bis allylamino pyrimidin-6-yl)-4-bis p.fluorobenzhydrylamino piperidine, M.P. (Kofler) of the corresponding dihydrochloride: 240° C. (anhydrous ethanol).

(55) 1-(4,6-bis allylamino s.triazin-2-yl)-4-p.fluorobenzhydrylamino-piperidine, M.P. (Kofler) of the corresponding dihydrochloride: 242° C. (anhydrous ethanol).

(56) 1-(4,6-bis allylamino s.triazin-2-yl)-4-(Δ3-chromen-3-yl methylamino piperidine, M.P. (Kofler) of the corresponding dihydrochloride: 242° C. (anhydrous ethanol).

(57) 1-(4,6-bis allylamino s.triazin-2-yl)-4-cinnamylamino piperidine, M.P. (Kofler) of the corresponding dihydrochloride: 195° C. (anhydrous ethanol).

(58) 1-(4,6-bis allylamino s.triazin-2-yl)-4-(4-fluoronaphth-1-yl methylamino)piperidine, M.P. (Kofler) of the corresponding difumarate. 217° C. (anhydrous ethanol).

(59) 1-(4,6-bis allylamino s.triazin-2-yl)-4-(benzothienyl-2 methylamino)-4 piperidine, M.P. (Kofler) of the corresponding difumarate: 220° C. (ethanol at 95%).

(60) 1-(2,4-bis allylamino pyrimidin-6-yl)-4-cynnamylamino piperidine, M.P. (Kofler): 205° C. (ethanol).

(61) 1-(2,4-bis allylamino s.triazin-2-yl)-3-bis p.fluorobenzhydrylamino-piperidine, M.P. (Kofler) of the corresponding difumarate: 150° C. (anhydrous ethanol).

(62) 1-(4,6-bis allylamino s.triazin-2-yl)-4-(benzodioxin-6-yl methylamino)piperidine, M.P. (Kofler) of the corresponding difumarate: 220° C. (anhydrous ethanol).

(63) 1-(4,6-bis allylamino s.triazin-2-yl)-4-p.fluorocinnamylamino piperidine, M.P. (Kofler) of the corresponding difumarate 210° C. (anhydrous methanol).

(64) 1-(4,6-bis allylamino s.triazin-2-yl)-4-ethylamino piperidine, M.P. (Kofler): 125° C. (acetonitrile).

(65) 1-(2,4-bis allylamino pyrimidin-6-yl)-4-p.fluorocinnamylamino piperidine, M.P. (Kofler) of the corresponding difumarate: 195° C. (ethanol).

(66) 1-(4,6-bis allylamino s.triazin-2-yl)-4-(3,3-bis p.fluorophenyl allylamino)piperidine, M.P. (Kofler) of the corresponding difumarate: 228° C. (anhydrous ethanol).

(67) 1-(4,6-bis allylamino s.triazin-2-yl)-3-cinnamylamino piperidine, M.P. (Kofler) of the corresponding fumarate: 220° C. (ethanol).

(68) 1-(4,6-bis allylamino s.triazin-2-yl)-3-cinnamylamino pyrrolidine, M.P. (capillary) of the corresponding difumarate: 206°–209° C. (anhydrous ethanol).

We claim:

1. A compound selected from the group consisting of: disubstituted polymethylene imines of the formula I:

in which:

A is selected from the group consisting of saturated hydrocarbon radicals containing from 3 to 5 carbon atoms inclusive in straight and branched chain, the corresponding unsaturated hydrocarbon radicals containing one and two double bonds, and the corresponding mono- and di-hydroxy (saturated and unsaturated hydrocarbon radicals, n is selected from the group consisting of zero and the integers 1 and 2;

Y is selected from the group consisting of oxygen and a radical of the formula: N—$R_1$ in which $R_1$ is selected from the group consisting of hydrogen, alkyl and hydroxyalkyl each having from 1 to 5 carbon atoms inclusive, cycloalkyl and cycloalkenyl each having from 3 to 7 carbon atoms inclusive, and acetyl;

R is selected from the group consisting of: hydrogen, alkyl having from 1 to 5 carbon atoms inclusive, cycloalkyl having from 5 to 7 carbon atoms inclusive, unsubstituted phenyl and phenyl mono- and poly-substituted by a substituent selected from the group consisting of fluorine and chlorine; and B is selected from the group consisting of:

hydrogen, alkyl having from 1 to 5 carbon atoms inclusive, alkenyl having from 2 to 5 carbon atoms inclusive, phenyl, naphthyl, benzofuranyl, benzothienyl, benzodioxolyl, benzodioxanyl, benzodioxinyl, Δ3-chromenyl, thiochromenyl and chromanyl, and all these radicals mono- and poly-substituted by a substituent selected from the group consisting of fluorine and chlorine and alkyl and alkoxy each having from 1 to 5 carbon atoms inclusive, and a radical of the formula:

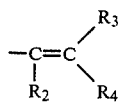

in which $R_2$, $R_3$ and $R_4$ which are the same or different, are each selected from the group consisting of hydrogen, unsubstituted phenyl and phenyl mono- and poly-substituted by a substituent selected from the group consisting of chlorine and fluorine; and physiologically tolerable acid addition salts thereof.

2. A compound of claim 1 which is 1-(4,6-bis allylamino s.triazin-2-yl)-4-bis p.fluorobenzhydrylamino piperidine, and its difumarate.

3. A compound of claim 1 in which is 1-(4,6-bis allylamino s.triazin-2-yl)-4-p.fluorobenzhydrylamino piperidine, and its dihydrochloride.

4. A compound of claim 1 which is 1-(4,6-bis alkylamino s.triazin-2-y)-4-ethoxy piperidine, and its difumarate.

5. A compound of claim 1 which is 1-(4,6-bis allylamino s.triazin-2-yl)-4-(benzofuran-2-yl methylamino)piperidine, and its hydrochloride.

6. A compound of claim 1 which is: 1-(4,6-bis allylamino s.triazin-2-yl)-4-p.fluorocinnamylamino piperidine, and its difumarate.

7. A pharmaceutical composition, suitable for use in the treatment of hypoxia, containing as active ingredient a compound of claim 1, in an amount effective for such purpose, together with a suitable pharmaceutical carrier.

8. A method for treating a living animal body afflicted with a tissular hypoxia, comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,514,398

DATED : April 30, 1985

INVENTOR(S) : Gilbert Regnier, Alain Dhainaut, Michel Laubie & Jacques Duhault

It is certified that error appears in the above-identified patent and that said Letters Patent is hereby corrected as shown below:

Title page, [56] References Cited, OTHER PUBLICATIONS, line 2; "p. 21;" should read -- p. 22; --

Col. 2, line 55; after "radicals" insert -- having --
Col. 6, line 26; "ar" should read -- at --
Col. 6, line 30; "allymino pydimidin-" should read -- allylamino pyrimidin- --
Col. 9, the formula under "Example 40", right hand side of the formula; "CH" should read -- $CH_2$ --
Col. 9, line 63; "alumimium" should read -- aluminium --
Col. 9, line 63; "rinced" should read -- rinsed --
Col. 10, line 61; "1-(4-bis" should read -- 1-(4,6-bis --
Col. 11, line 6; "s.triazin-2-yl-4-bis" should read -- s.triazin-2-yl)-4-bis --
Col. 11, line 26; "-4-benzyhy-" should read -- -4-benzhy- --
Col. 11, line 65; "1-(2,4-bis" should read -- 1-(4,6-bis --
Col. 14, line 1; delete "in"
Col. 14, line 4; "alkyl-" should read -- allyl- --

Signed and Sealed this

Twenty-sixth Day of November 1985

[SEAL]

Attest:

DONALD J. QUIGG

Attesting Officer

Commissioner of Patents and Trademarks